United States Patent [19]
Bathe et al.

[11] Patent Number: 6,089,229
[45] Date of Patent: Jul. 18, 2000

[54] HIGH CONCENTRATION NO PULSE DELIVERY DEVICE

[75] Inventors: Duncan P. L. Bathe, Madison; Frederick J. Montgomery, Sun Prairie, both of Wis.

[73] Assignee: Datex-Ohmeda, Inc., Madison, Wis.

[21] Appl. No.: 09/084,724

[22] Filed: May 26, 1998

[51] Int. Cl.[7] .................................................. A61M 16/00
[52] U.S. Cl. ................... 128/204.21; 128/203.12
[58] Field of Search ............... 128/203.12, 203.22, 128/204.23, 207.18, 204.26, 205.11, 206.11, 204.21

[56] References Cited

U.S. PATENT DOCUMENTS

| | | | |
|---|---|---|---|
| 4,705,034 | 11/1987 | Perkins | 128/203.12 |
| 4,832,014 | 5/1989 | Perkins | 128/203.12 |
| 4,919,128 | 4/1990 | Kopala | 128/207.18 |
| 4,932,401 | 6/1990 | Perkins | 128/203.12 |
| 4,989,599 | 2/1991 | Carter | 128/207.18 |
| 5,099,836 | 3/1992 | Rowland | 128/204.23 |
| 5,558,083 | 9/1996 | Bathe | 128/203.12 |
| 5,651,358 | 7/1997 | Briend et al. . | |

FOREIGN PATENT DOCUMENTS

95/10315  4/1995  WIPO .

OTHER PUBLICATIONS

Delivery and Monitoring of Inhaled NO in Patients with Pulmonary Hypertension, Critical Care Medicine, vol. 22, No. 6 (Jun., 1994), pp. 930–939.

Inhaled nitric oxide in persistent pulmonary hypertension of the newborn and Low–dose inhalational nitric oxide in persistent pulmonary hypertension of the newborn—The Lancet, vol. 340; Oct. 3, 1992 pp. 818–820.

Inhaled nitric oxide, the Past, the Present, and the Future—Anesthesiology, vol. 78, No. 3, Mar. 1993, pp. 413–416.

Pulsed Delivery of Inhaled Nitric Oxide to Patients with Primary Pulmonary Hypertension—Chest, vol. 109, Jun. 1996, pp. 1545–1549.

*Primary Examiner*—Aaron J. Lewis
*Assistant Examiner*—Teena Mitchell
*Attorney, Agent, or Firm*—Andrus, Sceales, Starke & Sawall

[57] ABSTRACT

A respiratory therapy apparatus that delivers a predetermined pulsed dose of a therapeutic gas to a patient upon inhalation of the patient. The system has separate conduits for the supply of the therapeutic gas at a high concentration and for the supply of a diluent gas. The therapeutic gas conduit has a control valve that is accurately controlled to open and close so as to deliver a precise dose of the high concentration therapeutic gas. The diluent gas conduit has means to ensure there is sufficient flow of diluent gas to ensure the said high concentration therapy gas is diluted to a safe concentration. A third conduit receives the gases from both the first and second conduits so that the gases are mixed together and administered to the patient. By this system, the therapeutic gas supply can be of a high, otherwise harmful, concentration and the therapeutic gas is diluted prior to introduction to the patient. The therapeutic gas may be nitric oxide and the diluent gas may be nitrogen or an oxygen containing gas.

23 Claims, 4 Drawing Sheets

HIGH CONCENTRATION NO PULSE DELIVERY DEVICE

BACKGROUND

This invention relates to the administration of a therapeutic gas such as nitric oxide (NO) to patients for therapeutic effect. In particular, it relates to a system wherein a controlled, predetermined supplemental volume of a dose of NO is provided to the patient with each inhalation by the patient.

The function of the administration of NO has been fairly widely published and typical articles appeared in The Lancet, Vol. 340, October 1992 at pages 818–820 entitled "Inhaled Nitric Oxide in Persistent Pulmonary Hypertension of the Newborn" and "Low-dose Inhalational Nitric Oxide in Persistent Pulmonary Hypertension of the Newborn" and in Anesthesiology, Vol. 78, pgs. 413–416 (1993), entitled "Inhaled NO-the past, the present and the future".

The actual administration of NO is generally carried out by its introduction into the patient as a gas and commercially available supplies are provided in cylinders under pressure and may be at pressures of about 2000 psi and consist of a predetermined mixture of NO in a carrier gas such as nitrogen. A pressure regulator is therefore used to reduce the pressure of the supply cylinder to working levels for introduction to a patient.

The concentration administered to a patient will vary according to the patient and the need for the therapy but will generally include concentrations at or lower than 100 ppm. There is, of course, a need for that concentration to be precisely metered to the patient since an excess of NO can be harmful to the patient.

Various delivery devices have been used or suggested that respond to the patient attempting to inhale to deliver a pulsed dose of NO to the patient and such pulsing devices have also been shown to have therapeutic effect on the patient, for example, as described in Higenbottam PCT patent application WO 95/10315 and the publication of Channick et al "Pulsed delivery of inhaled nitric oxide to patients with primary pulmonary hypertension", Chest/109/ June 1996. In such pulsatile dosing devices, a pulse of NO is administered to the patient as the patient inhales spontaneously.

One difficulty of the present pulsed NO devices is that the concentration of the NO used by the systems, and which is commercially supplied in pressurized cylinders mixed in nitrogen, is relatively low since high concentrations of NO are injurious to patients. Therefore the devices use NO gas mixed in nitrogen with a concentration of NO of about 100 ppm. Thus, large supplies of the NO containing therapy gas cylinders are required to treat the patient rather than a lesser quantity of a high concentration of NO in nitrogen of about 800 ppm which can then be diluted down to about 100 ppm to be able to administer the proper dosage to the patient. In addition if all of the balance gas for NO is nitrogen, the amount of non-oxygenated gas that the patient receives per breath is increased and therefore, the potential of delivering a hypoxic breath exists.

There are certain devices that carry out the blending of the NO containing gas with a diluent or mixing gas and one such system is shown and described in Wessel et al, Delivery and Monitoring of Inhaled NO in patients with pulmonary hypertension (Critical Care Medicine, Vol. 22, No. 6 1995). In the Wessel et al system, however, the medical NO is blended with nitrogen through the use of medical blenders that require continuous flows of all the gases to properly blend the gases together prior to administration to the patient or to a ventilator.

In another system, that of Briend et al, U.S. Pat. No. 5,651,358, pulsed injections of NO are administered into a ventilator circuit using a delivery device that is triggered by a signal from the respirator.

A further device for the pulsed administration of NO has been developed and which is described in copending U.S. Ser. No. 08/857,924 filed May 16, 1997 and the disclosure of which is incorporated herein by reference. In that further system, the actual pulse of NO is corrected for ambient conditions to assure that the dose of the NO pulse is precise and does not vary depending upon differing ambient conditions.

Accordingly it would be desirable to provide a pulsing device that enables one to use a patient initiated breath that would administer a safe, diluted therapeutic mixture of NO during the patient's inhalation yet be able to use, as the supply of NO, a relatively high concentration of NO in a gas such as nitrogen and the NO mixed with a diluent gas on a pulse to pulse basis.

SUMMARY OF THE INVENTION

In accordance with the invention, there is provided a nitric oxide pulse delivery system where a supply of a relatively high concentration of NO in a carrier gas such as nitrogen can be used as the source of NO to be eventually delivered to the patient. In the invention, that high concentration supply of NO is diluted by a separate supply of a diluent gas, such as nitrogen or oxygen containing gas, provided by means of a pressurized supply cylinder or a concentrator that extracts the nitrogen or oxygen containing gas from the atmosphere.

In the present pulse device, the system activates upon the patient attempting to inhale and that sensed inhalation triggers the pulse device to provide a precise volume of NO containing therapeutic gas to the patient. The high concentrated NO containing gas can be supplied by a pressurized gas cylinder and which is mixed with a diluent gas to reduce that of NO down to an acceptable, safe level for administration to the patient. The system acts on a pulse to pulse basis to give that patient a precise dose of a NO containing gas having a safe concentration and in a precise, known dose upon each inhalation of the patient.

If the diluent is an oxygen containing gas it is administered to the patient through a means such as a split nasal cannula where the mixing of the NO containing gas and the oxygen containing gas takes place within the cannula, in any event, immediately prior to introduction into the patient.

A central processing unit (CPU) controls the open time of a control valve that controls the flow of the high concentration NO containing gas through the system to provide a precise known dose of that gas. At the same time, a similar, parallel system, under the control of the same CPU provides a separate precise dose of a diluent gas. The high concentration supply of the NO gas and the diluent gas are then mixed together to form a precise dose of a mixed gas having the NO concentration reduced to a safe level for administration to the patient. The CPU opens the control valves to admit the high concentration supply of NO containing gas and the supply of the diluent gas from their normally closed positions for a calculated period of time upon the system sensing the patient attempting to inhale. The gases from each of the control valves are then mixed and supplied to the patient.

At the end of a predetermined time period, the CPU switches the control valves from their energized, open positions, back to the de-energized, closed position. The flow of both the high concentration NO containing gas and the diluent gas flows through fixed restrictors that are located intermediate to the control valves and the patient. The amount of the time during which the control valves are open is calculated by the CPU based on the mass flow through the control valves, measured using the pressure and temperature of the gases delivered through the restrictors and the characteristics of the fixed restrictors. This mass flow can be corrected to volume flow using ambient temperature and pressure if the required dose is a volume. The amount of time during which the control valves are open can be corrected to the predetermined desired doses of the gases based on the measured values and the concentration of the NO containing therapeutic gas to be delivered to the patient. The diluent control valve is opened for a time at least the same as the NO control valve is open. The amount of dilution is governed by the ratio of the flows through the fixed restrictors. As an example, if the high NO concentration gas has a concentration of 800 ppm of NO and the desired concentration to the patient is 100 ppm of NO, the flow through the fixed restrictors is set at a ratio of at least 7:1. The device then delivers a volume of 800 ppm NO gas that is diluted to give an equivalent dose of 100 ppm NO to the patient.

The system determines the volume of the high concentration of NO containing gas and the volume of the diluent gas. As can then be seen, given the volumes so determined, the delivered volumes can be compared to the predetermined desired doses set by the user or established in the delivery system and the control valves open times varied by the CPU to correct for any differences.

In addition, as the system knows the doses of NO and the diluent gases delivered it can alarm to the user a potential hazard associated with NO delivery, that is, over and under delivery of NO.

The system can also alarm the user to the potential hazard associated with high levels of NO2, a toxic substance that is formed when NO reacts with oxygen. The amount of NO2 formed is dependent on the concentration of NO the concentration of oxygen and the amount of time the gases are together before the mixture is administered to the patient, as each of these parameters can be known by the system an appropriate alarm can be given when unsafe levels of NO2 are present.

Thus, a supply cylinder of high concentration NO containing gas is used and is diluted precisely to form a predetermined, accurate, pulsed dose of diluted NO containing gas to be delivered to the patient as a pulse each time that the patient inhales.

DETAILED DESCRIPTION OF THE INVENTION

Figure 1:
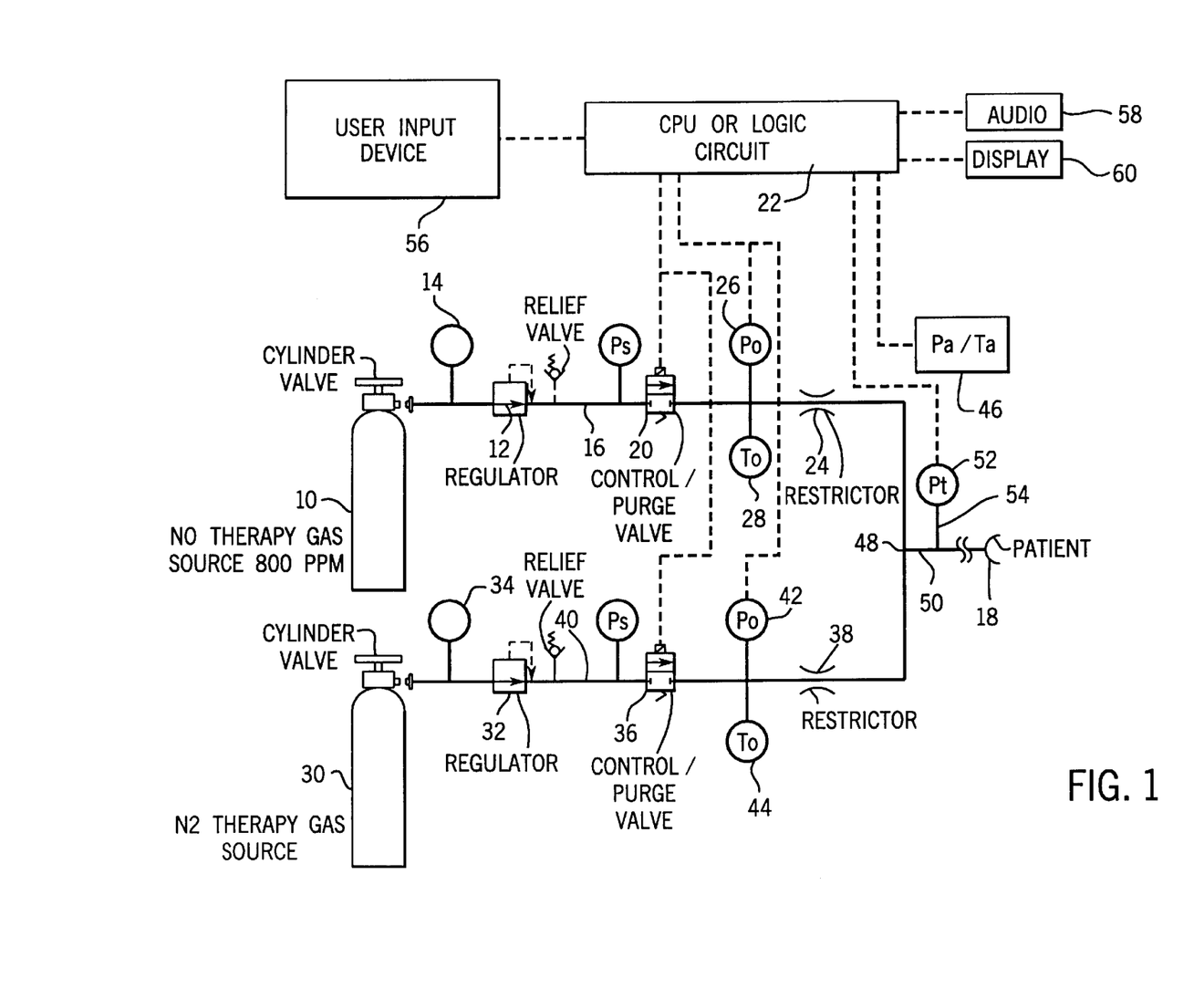
FIG. 1 is a schematic view of a NO delivery system constructed in accordance with the present invention where the diluent is nitrogen.

Turning now to FIG. 1, there is shown a schematic view of a pulsed dosing NO delivery apparatus constructed in accordance with the present invention where the diluent is nitrogen. A gas cylinder 10 is provided containing the nitric oxide mixed with a balance or carrier gas such as nitrogen and the NO concentration is of a relatively high concentration of about 800 ppm of NO in the carrier gas. Such concentration, if administered directly to a patient, would be a toxic level. The NO can be supplied in pressurized cylinders of the gas at pressures of approximately 2000 psig.

Following the flow of that gas through the delivery system, therefore, a pressure regulator 12 reduces the cylinder pressure down to a working pressure for use with the present system and that pressure may be in the order of about 50 psig. A pressure gauge 14 is generally provided on the pressure regulator 12 in order to monitor the pressure within the gas cylinder 10.

The high concentration NO containing therapy gas passes through a conduit 16 and which channels that gas through the NO pulse delivery system where it is eventually administered to the patient 18 by means such as a nasal cannula.

A control valve 20 controls the flow of high concentration NO containing therapy gas from the gas cylinder 10 to the patient 18 and is a solenoid controlled valve operated by signal from the CPU 22. Again, for safety, the control valve 20 is normally closed and is moved to its open position when a signal energizes the valve by CPU 22. As will be explained, the time during which the control valve 20 is in the open position controls the dose of NO containing therapy gas to the patient 18.

A fixed restrictor 24 is also provided in the conduit 16 and may be a commercially available restrictor and which is provided with the pressure to flow characteristics by the supplier. Just upstream of the fixed restrictor 24 is an absolute pressure transducer 26 which senses the absolute pressure in the conduit 16 as $P_o$. That pressure is also communicated to the CPU 22 as will be later explained. The absolute pressure transducer 26 is of the type that operates off a base of zero psi and therefore it reads the absolute pressure within the conduit 16 at the point just upstream of the fixed restrictor 24. Typical pressure transducers of the absolute pressure type are available from Sensyn, Inc. A temperature sensor 28 is also located just upstream of the fixed restrictor 24 and provides a temperature $T_o$. Accordingly, there are signals representative of the pressure and the temperature of the gas at a point just upstream of the fixed restrictor 24 that are provided as inputs to the CPU 22.

A similar flow path is provided for the diluent gas that is supplied from diluent gas cylinder 30. As noted, that diluent gas may be nitrogen or various other gases that are not harmful to a patient and which can be used as a means of diluting the high concentration of NO therapeutic gas from the gas cylinder 10. The supply of nitrogen may be by means of the gas cylinder 30 or may be provided by a nitrogen concentrator where nitrogen is separated from the surrounding atmosphere.

Continuing on the flow path of the diluent gas, the same components to the gas stream can be used as in the stream of the NO containing gas and include a pressure regulator 32, and a pressure gauge 34. Again, a control valve 36 is present and which is controlled by the CPU 22 to open and close based on signals from that CPU 22. A fixed restrictor 38 is located in the conduit 40 and a pressure transducer 42 determines $P_o$ and temperature sensor 44 senses the temperature $T_o$ in the conduit 40 just upstream of the fixed restrictor 38.

Further pressure and temperature sensors are used to determine the ambient pressure and temperature and those sensors are represented by block 46 and those ambient conditions are supplied to the CPU 22 in order to compensate for the particular ambient conditions at the location where the system is being used to allow the dose to be calculated as volume Accordingly, as may now be seen, the CPU 22 is in receipt of all of the information necessary to determine the exact flow of NO containing therapy gas and diluent gas through the fixed restrictors 24 and 38, respectively. Since the flow path of the NO containing gas and the diluent gas are the same, only the flow path controlling the NO containing gas will be described. The characteristics of the particular fixed restrictor 24, as stated, are available from the manufacturer as a curve or other data that can be inputted to the CPU 22 as a look up table or the like. Since the mass flow through the fixed restrictor 24 is directly proportional to the absolute pressure of the gas and inversely proportional to the square root of the temperature of the gas entering the fixed restrictor 24, the CPU 22 knows the value of $P_o$ from the absolute pressure transducer 26 and the value of the $T_o$ from temperature sensor 28 and thus can readily calculate the mass flow through the conduit 16, that is, the mass flow of the high concentration NO containing gas. This mass flow can be corrected to the ambient condition and represent a volumetric flow using ambient pressure and temperature transducers 46.

Thus, the flow and thus the volume of gas being delivered through conduit 16, and likewise conduit 40 through the same computation is known and the respective known volumes are mixed in a confluence 48 to combine the known volume of high concentration NO containing gas and the known volume of diluent gas such as nitrogen, to give an equivalent dose of NO at a safe concentration. Thus, a conduit 50 then channels that mixed gas from the confluence 48 to the patient 18. That mixed gas is of a known dose and, of course, a known concentration of NO. As stated, that concentration is about 100 ppm or less to the patient and is considerably less than the possible 800 ppm NO containing gas that is originally present in the gas cylinder 10.

A patient trigger 52 is in communication with the patient 18 by means of a passageway 54 and may be of conventional design. The patient trigger 52 detects a negative pressure $P_T$ from the patient 18 indicating that the patient 18 is initiating inhalation and provides a signal to the CPU 22 to alert the CPU 22 that the patient is initiating an inhalation. Upon receipt of that signal, the CPU 22 can take the appropriate action to open the control valves 20 and 36 to provide a pulse of NO containing therapeutic gas to the patient 18 during that inhalation.

A user input device 56 allows the user to input to the CPU 22 the specific dose of NO containing therapeutic gas at a safe concentration that is desired to be delivered to the patient 18 during each inhalation and such device may be a rotary switch or the like. Alternatively, the dose to be delivered may be predetermined by the manufacturer of the delivery system and already established in the system and not be individually selected in the field by a user. User input device 56 may also indicate the ON/OFF status of the NO pulse delivery device. Also, as a part of the system, there may be an audio alarm 58 and a visual display 60 that may also contain visual alarms as well as display various monitored conditions of the device to the user.

The overall operation of the NO dosing device may now be explained and will refer to the delivery system embodiment where the user makes the desired selection of the dose to be administered to the patient. As noted, upon start-up of the system, the gas cylinder 10 containing the NO therapy gas at the high concentration is opened and the NO containing therapy gas enters the pressure regulator 12 and the conduit 16. Similarly, the diluent gas cylinder 30 is opened to cause that gas to enter the conduit 40.

The user inputs a dose of NO containing therapy gas at a safe concentration that is desired to be administered to the patient 18 by means of the user input device 56. As the patient initiates an inhalation, the patient trigger 52 senses the negative pressure and signals the CPU 22 to commence the injection of a dosage of NO containing therapy gas to the patient 18. Initially, the CPU 22 opens the control valves 20 and 36 for a period of time calculated by the CPU 22 based on the dose inputted by the user, Vset. That open time, $T_{INITIAL}$, is based on the curves that were established upon the calibration conditions at the factory in initially setting up the system. The system, as manufactured, is calibrated to determine the volumes delivered for the times the control valves 20 and 36 are open and is operated at the conditions in the manufacturing facilities during calibration, that is $T_{CAL}$ and $P_{CAL}$ and a set of curves generated for the system.

In use, therefore, as the patient attempts to inhale, the CPU 22 has information from transducers 46 with respect to the ambient pressure $P_A$ and the ambient temperature $T_A$ and can calculate the $V_{CAL}$ that needs to be provided to the patient for the dose inputted by the user, Vset, based on the actual ambient conditions existing at the patient. Thus, by use of the equation:

$$V_{CAL}=(P_A/P_{CAL})*(T_{CAL}/T_A)*V_{SET}$$

the CPU can determine the $V_{CAL}$ and adjust to the ambient conditions to determine the time that the control valves 20 and 36 need to be opened to deliver the $V_{SET}$ to the patient at those ambient conditions.

Again the dose actually delivered by the system can be determined as a check against the $V_{SET}$ by the measurements of the temperature of the gas passing through the fixed restrictors 24 and 38, the absolute pressure of the gas upstream of the fixed restrictors 24 and 38 and the known pressure flow characteristics of the restrictor or orifice. Thus, by use of the equation:

$$V_{DEL}=k2.\int\{(P_O/P_A).T_A/(T_O)^{0.5}\}.dt$$

Where:

$V_{DEL}$=the volume of the pulse where the flow through the orifice was sonic k2=constant for the orifice geometry and gas characteristics $P_O$=orifice gas pressure $T_O$=orifice gas temperature $P_A$=ambient pressure $T_A$=ambient temperature The actual delivered flow can be determined and integrated with the time the control valve is in the open position to derive the $V_{DEL}$ to the patient. The volume delivered can then be compared with the volume established by the user $V_{SET}$ and any error between the values can be used to modify the $T_{INITIAL}$ to become $T_{CONTROL}$ that will correct for any differences.

As a further feature of the present invention, an alarm strategy is used to insure that the delivery device is properly delivering the dose that is desired and inputted by the user. In the implementation of the alarm system, that dose actually delivered by the system, $V_{DEL}$ as compared with the $V_{SET}$ can be used to trigger an alarm if the values are different by a predetermined percentage. That is, if the actual delivered dose is more that a certain percentage, for example, thirty percent (30%), or the concentration of NO is higher than a safe level, say 100 ppm, the CPU 22 can recognize that the difference is indicative of a problem in the overall pulse delivery system and trigger the audible alarm 58 and/or provide some visual alarm on the visual display 60.

Figure 2:
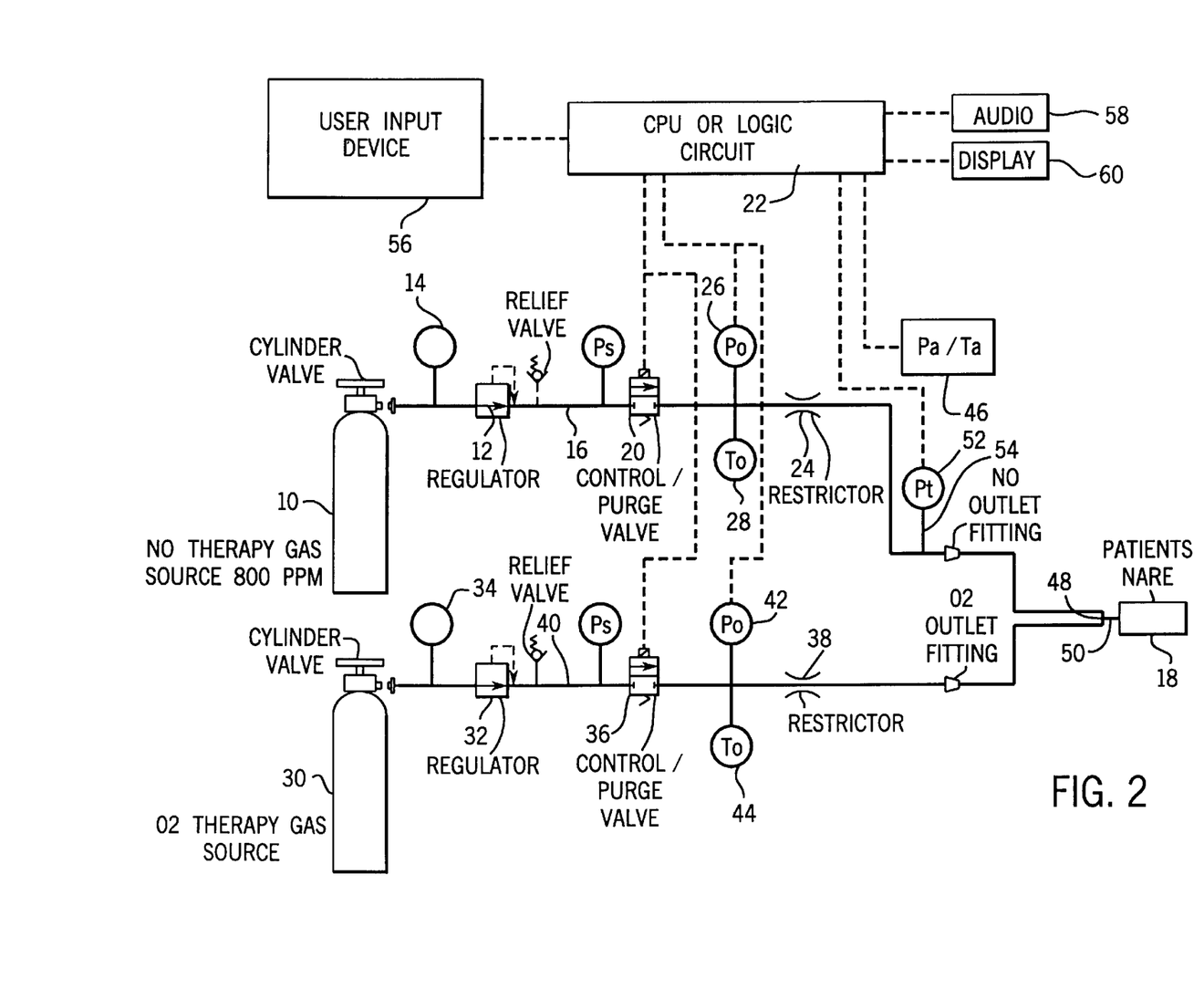
FIG. 2 is a schematic view of the present invention where the diluent is an oxygen containing gas.

Turning now to FIG. 2, there is shown a schematic view of the preferred embodiment of the present invention wherein the diluent is an oxygen containing gas and the point of confluence 48 is at or directly prior to the introduction of the NO containing therapeutic gas to the patient. This is important as it reduces the time that the NO can oxidize and form NO2, a toxic compound. In FIG. 2, therefore, the point of confluence 48 is located just prior to the actual introduction into the patient and the patient trigger 52 is located upstream of the point of confluence 48.

The overall operation of the device is similar to that explained above for the device with the diluent being nitrogen. In addition to the user inputting the desired NO dose the user may also input a desired oxygen dose. If this dose exceeds the minimum volume required to dilute the NO dose to a safe concentration the CPU 22 will continue to energize control valve 36 for a time that is sufficient to accurately deliver the user inputted desired oxygen dose. The actual delivered oxygen dose is measured using the same principles as that for the delivered NO dose.

Again as a further feature of this device, an alarm strategy is used to insure that the delivery device is properly delivering the dose of NO that is desired and inputted by the user as described above, and additionally that the oxygen dose that is desired by the user is also properly delivered. That is, if the actual delivered dose of the oxygen is more than, or less than a certain percentage, for example, thirty percent (30%), the CPU 22 can recognize that the difference is indicative of a problem in the overall pulse delivery system for oxygen and trigger the audible alarm 58 and/or provide some visual alarm on the visual display 60.

Figure 3:
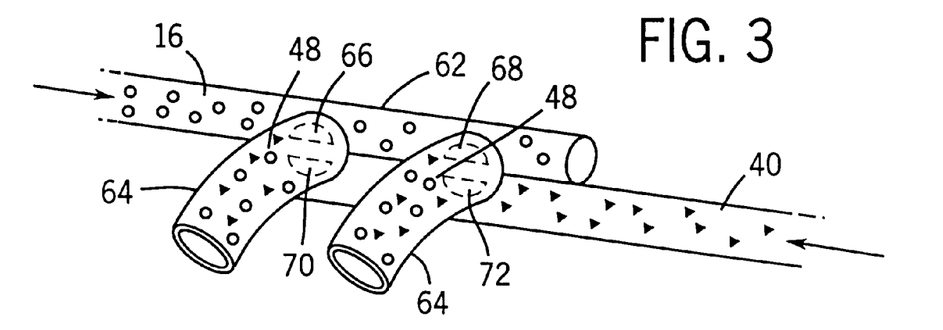
FIG. 3 is a perspective view of a split nasal cannula that can be used with the present invention.

In FIG. 3, there is shown an isometric view of a split nasal cannula 62 that can be used with the embodiment of FIG. 2. The split nasal cannula 62 thereby positions the point of confluence such that the mixing of the NO containing gas and the oxygen containing diluent gas occurs within the split nasal cannula 62 by means of the conduit 16 and the conduit 40 supplying the high concentration NO gas and the diluent oxygen containing gas, respectively, to the split nasal cannula 62. As can be seen the NO gas enters both of the nasal prongs 64 by openings 66 and 68 and the diluent oxygen containing gas also enters the nasal prongs 64 through openings 70 and 72 such that the mixing of the oxygen containing gas and the high concentration NO containing gas takes place in the split nasal cannula 62 to be administered to the nostrils of the patient through the nasal prongs 64. By having the mixing or confluence 48 at the point of introduction to the patient, the oxygen and the NO are in mixture only a minimum amount of time so that the possibility of a harmful formation of any significant amount of toxic $NO_2$ is prevented.

Figure 4:
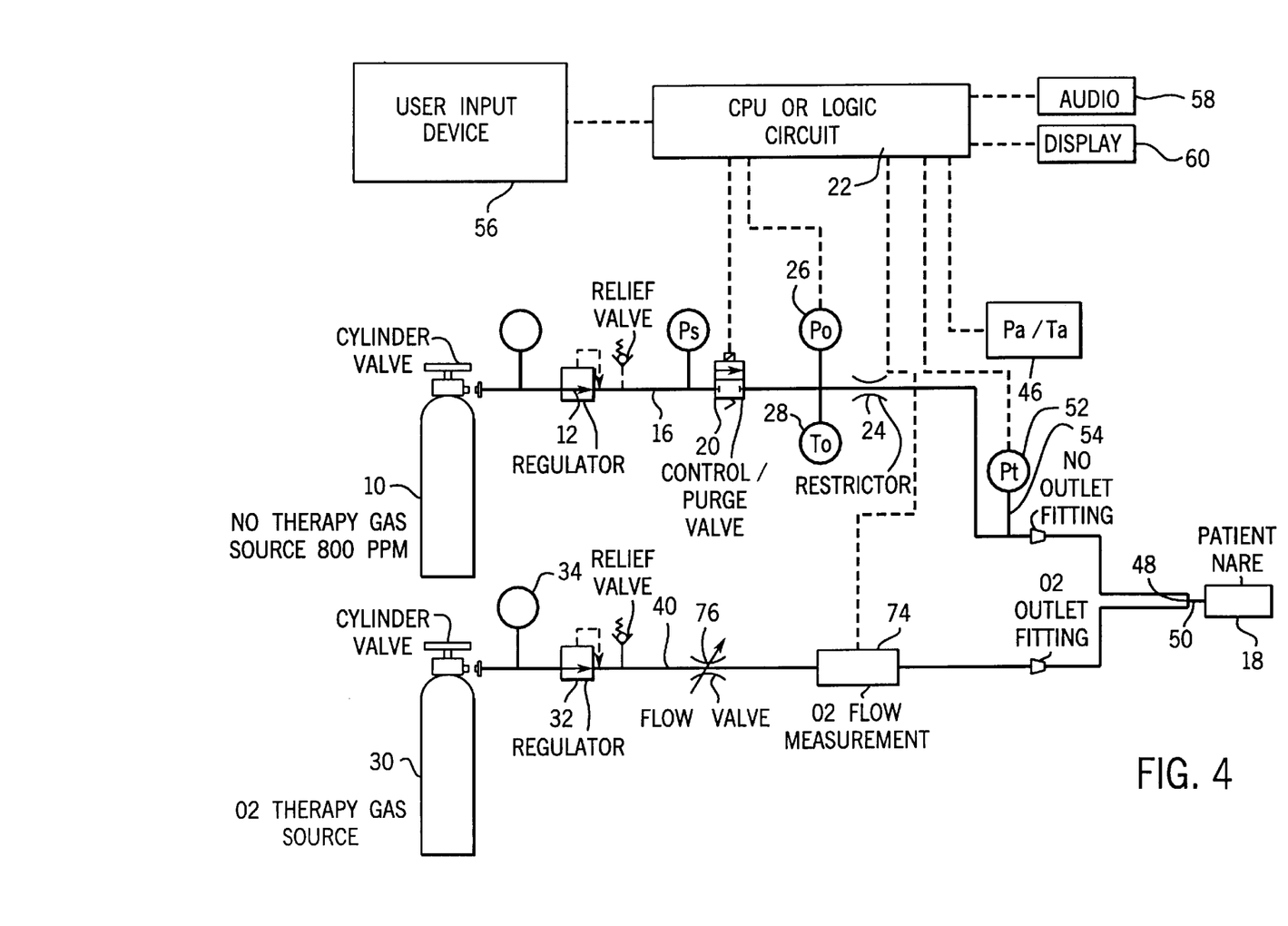
FIG. 4 is a schematic view of an alternative embodiment of the present invention.

Finally, turning to FIG. 4, there is shown a schematic view of a further embodiment of the present invention wherein a flow sensor 74 is positioned in the conduit 40 containing the diluent gas. That flow sensor 74 determines the flow in the conduit 40 as metered by the variable flow restrictor 76. In this embodiment, only one solenoid activated control valve 20 is used to pulse the high concentration NO containing gas and is controlled by the CPU 22. The flow sensor 74 determines that a predetermined minimum flow is being supplied through the variable flow restrictor 76. If that minimum flow is available, a signal is communicated to the CPU 22 to allow a pulse of high concentration NO containing gas to be provided through conduit 16 by means of a control valve 20 actuated from the CPU 22. If that minimum flow is not flowing through the flow sensor 74, the CPU 22 is notified that no pulse of NO containing gas can be administered and the control valve 20 is prevented from opening.

In this manner, only the control valve 20 is controlled by the CPU 22 to provide a predetermined dose of gas containing NO to the patient while the other conduit 40 supplying the diluent gas needs to be supplying a minimum flow to assure that the high concentration NO containing gas is properly diluted to achieve the correct concentration of NO to be administered to the patient.

Numerous further variations and combinations of the features discussed above can be utilized without departing from the spirit of the invention as defined by the claims below. Accordingly, the foregoing description of the preferred embodiment should be taken by way of illustration rather than by way of limitation of the invention as claimed.

We claim:

1. A respiratory therapy apparatus for delivering a pulse dose of a therapeutic gas to a patient at a safe concentration, said apparatus comprising:

means connecting said respiratory therapy apparatus to a source of a high concentration therapeutic gas, means connecting said respiratory therapy apparatus to a source of a diluent gas, means to establish a predetermined desired pulse dose of therapeutic gas, sensing means for sensing the initiation of an inhalation of a patient, delivery means having a first state and a second state, said delivery means delivering a pulse of high concentration therapeutic gas when said delivery means is in said second state, said delivery means being responsive to said sensing means for sensing the initiation of an inhalation of a patient and controlling the amount of time said delivery means is in the second state to deliver a pulse of said high concentration therapeutic gas during the inhalation of the patient for mixing with said diluent gas;

flow measurement means for measuring the flow of said diluent gas to a patient, and means responsive to said flow measurement means for providing a sufficient flow of said diluent gas to a patient to ensure said high concentration of therapeutic gas is diluted to a safe concentration when mixed with said diluent gas.

2. A respiratory therapy apparatus for delivering a pulse dose of a therapeutic gas to a patient as defined in claim 1 wherein said high concentration therapeutic gas is nitric oxide.

3. A respiratory therapy apparatus for delivering a pulse dose of a therapeutic gas to a patient as defined in claim 1 wherein said diluent gas is nitrogen.

4. A respiratory therapy apparatus for delivering a pulse dose of a therapeutic gas to a patient as defined in claim 1 wherein said diluent gas is an oxygen containing gas.

5. A respiratory therapy apparatus for delivering a pulse dose of a therapeutic gas to a patient as defined in claim 1 wherein said means for providing a sufficient flow of said diluent gas comprises a delivety means to deliver a flow of diluent gas at a sufficient flow rate to ensure a safe concentration of therapeutic gas.

6. A respiratory therapy apparatus for delivering a pulse dose of a therapeutic gas to a patient as defined in claim 5 wherein said high concentration therapeutic gas is nitric oxide.

7. A respiratory therapy apparatus for delivering a pulse dose of a therapeutic gas to a patient as defined in claim 6 wherein said diluent gas is oxygen.

8. A respiratory therapy apparatus for delivering a pulse dose of a therapeutic gas to a patient as defined in claim 1 including an alarm activated when said diluent gas flow is insufficient to ensure said high concentration therapeutic gas is diluted to a safe concentration of therapeutic gas.

9. A respiratory therapy apparatus for delivering a pulse dose of a therapeutic gas to a patient as defined in claim 1 including means to inactivate the said therapeutic gas delivery means when said diluent gas flow is insufficient to ensure said high concentration therapeutic gas is diluted to a safe concentration of therapeutic gas.

10. A respiratory therapy apparatus for delivering a pulse dose of a therapeutic gas to a patient as defined in claim 1 wherein said means for providing a sufficient flow of diluent gas to a patient is further defined as providing a pulsatile flow of diluent gas.

11. A respiratory therapy apparatus for delivering a therapeutic gas to a patient at a safe concentration, said apparatus comprising;
   a first conduit adapted to be connected to a source of high concentration therapeutic gas under pressure,
   a second conduit adapted to be connected to a source of a diluent gas,
   a nasal cannula adapted to be connected to said first and said second conduits for receiving gas from both of said conduits and having a mixing chamber for mixing the gas from said first conduit and the gas from said second conduit,
   said cannula having a prong means for immediately delivering the mixed gas from said mixing chamber into a patient,
   delivery means to deliver a high concentration of therapeutic gas during the inhalation of the patient; and
   delivery means to deliver a sufficient flow of said diluent gas to ensure said high concentration therapeutic gas is diluted to a safe concentration in mixed gas.

12. A respiratory therapy apparatus for delivering a therapeutic gas to a patient as defined in claim 11 wherein said diluent gas is an oxygen containing gas.

13. A respiratory apparatus for delivering a therapeutic gas to a patient as defined in claim 11 wherein said therapeutic gas includes nitric oxide.

14. A respiratory therapy apparatus for delivering a therapeutic gas to a patient as defined in claim 11 wherein said prong means comprises a pair of nasal prongs that each contain a mixing chamber and which introduce the mixed gas directly into the nostrils of a patient.

15. A respiratory therapy apparatus for delivering a therapeutic gas to a patient as defined in claim 11 wherein said delivery means are control valves having both open and closed positions for delivering pulses of therapeutic gas and diluent gas and wherein the position of said control valves is controlled by a processor.

16. A respiratory therapy apparatus for delivering a therapeutic gas to a patient as defined in claim 15 further comprising a means to sense when a patient is attempting to inhale to provide a signal to said processor and wherein said processor signals said control valves to said open positions based upon said signal indicating inhalation by a patient.

17. A respiratory therapy apparatus for delivering a pulse dose of nitric oxide to a patient at a safe concentration using a diluent gas, said apparatus comprising:
   a first conduit adapted to be connected to a source of high concentration nitric oxide gas;
   a second conduit adapted to be connected to a source of diluent gas;
   first delivery means to deliver a pulse of high concentration nitric oxide gas along said first conduit during inhalation by a patient;
   second delivery means to deliver a sufficient flow of the diluent gas along said second conduit to ensure the high concentration nitric oxide gas pulse is diluted to a safe concentration;
   means coupled to said first and second conduits for forming a point of confluence for said high concentration nitric oxide gas and said diluent gas from said conduits, the confluence of such gases mixing and diluting said high concentration nitric oxide gas in said diluent gas to provide a safe concentration of nitric oxide and form the pulse dose of nitric oxide; and
   third conduit means extending from said point of confluence to a point of administration for a patient for flowing mixed gases to a patient, the location of the point of confluence with respect to the point of administration and such a length of the third conduit means being such as to minimize the time during which the mixture of gases exists prior to administration to a patient.

18. A respiratory therapy apparatus according to claim 17 further defined as delivering a pulse dose of nitric oxide to a patient at a safe concentration using an oxygen containing diluent gas while minimizing the formation of a nitrogen dioxide reaction product, and wherein said second conduit is adapted to be connected to a source of diluent gas containing oxygen.

19. A respiratory therapy apparatus for delivering a pulse dose of a therapeutic gas to a patient at a safe concentration, said apparatus comprising:
   first connecting means connecting said respiratory therapy apparatus to a source of high concentration therapeutic gas;
   second connecting means connecting said respiratory therapy apparatus to a source of diluent gas for supplying diluent gas to a patient;
   means for establishing a desired quantity of therapeutic gas as the pulse dose;
   means for sensing the amount of diluent gas supplied to a patient to ensure that the supply of diluent gas is sufficient to dilute said high concentration therapeutic gas to a safe concentration;
   delivery means coupled to said first connecting means, said delivery means having a first state and a second state, said delivery means delivering a quantity of gas as a pulse of high concentration therapeutic gas when in said second state;
   a sensor for sensing the initiation of inhalation by a patient;
   control means for controlling the amount of time said delivery means is in the second state and the quantity of gas delivered by said delivery means as a pulse when inhalation is sensed by said sensor; and
   measurement means for measuring the quantity of gas delivered by said delivery means, said measurement means being coupled to said control means to alter the quantity of gas delivered by said delivery means responsive to the measured quantity of gas so that the pulse dose delivered to a patient contains the desired quantity of therapeutic gas.

20. A respiratory therapy apparatus for delivering a pulse dose of a therapeutic gas to a patient as defined in claim 19 wherein said high concentration therapeutic gas is nitric oxide.

21. A respiratory therapy apparatus for delivering a pulse dose of a therapeutic gas to a patient at a safe concentration, said apparatus comprising:

first connecting means connecting said respiratory therapy apparatus to a source of high concentration therapeutic gas;

second connecting means connecting said respiratory therapy apparatus to a source of diluent gas for supplying diluent gas to a patient;

means for establishing a desired quantity of therapeutic gas as the pulse dose;

diluent gas flow measurement means for measuring the amount of diluent gas supplied to a patient to ensure that the supply of diluent gas is sufficient to dilute said high concentration therapeutic gas to a safe concentration;

delivery means coupled to said first connecting means, said delivery means having a first state and a second state, said delivery means delivering a quantity of gas as a pulse of high concentration therapeutic gas when in the second state; and control means coupled to said delivery means for controlling the amount of time said delivery means is in said second state and the quantity of gas delivered by said delivery means as the pulse, said control means being coupled to said diluent gas flow measuring means for operating said delivery means when a sufficient supply of diluent gas is present.

22. A respiratory therapy apparatus for delivering a pulse dose of a therapeutic gas to a patient as defined in claim 21 wherein said high concentration therapeutic gas is nitric oxide.

23. A respiratory therapy apparatus for delivering a pulse dose of therapeutic gas to a patient as defined in claim 21 further including means in said second connecting means for supplying said diluent gas in pulses of diluent gas.

* * * * *